US012751792B2

(12) United States Patent
Gregg et al.

(10) Patent No.: US 12,751,792 B2
(45) Date of Patent: Oct. 6, 2026

(54) DENTAL LASING DEVICE SYSTEM AND METHOD

(71) Applicant: MILLENNIUM HEALTHCARE TECHNOLOGIES, INC., Cerritos, CA (US)

(72) Inventors: Robert H. Gregg, Huntington Beach, CA (US); Dawn M. Gregg, Huntington Beach, CA (US); Austen R.H. Gregg, Huntington Beach, CA (US)

( * ) Notice: Subject to any disclaimer, the term of this patent is extended or adjusted under 35 U.S.C. 154(b) by 0 days.

(21) Appl. No.: 16/279,892

(22) Filed: Feb. 19, 2019

(65) Prior Publication Data

US 2019/0254775 A1 Aug. 22, 2019

Related U.S. Application Data

(60) Provisional application No. 62/631,949, filed on Feb. 19, 2018.

(51) Int. Cl.

| | |
|---|---|
| *A61C 1/00* | (2006.01) |
| *A61B 18/00* | (2006.01) |
| *A61B 18/20* | (2006.01) |
| *A61B 18/22* | (2006.01) |
| *A61B 34/00* | (2016.01) |
| *A61C 5/30* | (2017.01) |
| *A61C 8/02* | (2006.01) |
| *A61C 19/06* | (2006.01) |

(Continued)

(52) U.S. Cl.
CPC ............ *A61C 1/0046* (2013.01); *A61B 34/25* (2016.02); *A61C 1/0015* (2013.01); *A61C 5/30* (2017.02); *A61C 19/06* (2013.01); *A61N 5/0603* (2013.01); *A61B 2018/00047* (2013.01); *A61B 2018/00577* (2013.01); *A61B 2018/00589* (2013.01); *A61B 2018/00601* (2013.01); *A61B 2018/00642* (2013.01); *A61B 2018/0072* (2013.01); *A61B 2018/00779* (2013.01); *A61B 2018/00791* (2013.01); *A61B 2018/2025* (2013.01); *A61B 18/22* (2013.01); *A61B 2018/2205* (2013.01); *A61B 2018/225* (2013.01); *A61C 8/0006* (2013.01); *A61N 2005/0606* (2013.01); *A61N 5/0624* (2013.01); *A61N 2005/063* (2013.01); *A61N 2005/0651* (2013.01); *A61N 2005/0659* (2013.01); *A61N 2005/0663* (2013.01); *A61N 5/067* (2021.08)

(58) Field of Classification Search
CPC ..... A61C 1/0046; A61C 1/0015; A61C 19/06; A61C 8/0006; A61N 5/0603; A61N 5/0624
See application file for complete search history.

(56) References Cited

U.S. PATENT DOCUMENTS 4,979,180 A * 12/1990 Muncheryan ........... H01S 3/093 372/71
5,123,845 A * 6/1992 Vassiliadis ............. A61B 17/24 433/215

(Continued)

FOREIGN PATENT DOCUMENTS

EP 0941707 B1 5/2005
KR 20160033628 A * 3/2016

*Primary Examiner* — Amanda L Steinberg

(57) ABSTRACT

A diode laser system having high-power diode(s) said high-power diode(s) producing laser outputs in a range of 0.1 to 25 Watts of power using optimum wavelengths via a single optical delivery fiber.

14 Claims, 5 Drawing Sheets

(51) Int. Cl.

| | |
|---|---|
| ***A61N 5/06*** | (2006.01) |
| ***A61N 5/067*** | (2006.01) |

(56) References Cited

U.S. PATENT DOCUMENTS

| | | | | |
|---|---|---|---|---|
| 5,879,159 | A * | 3/1999 | Cipolla | H01J 61/86 362/183 |
| 6,918,762 | B2 | 7/2005 | Gill et al. | |
| 7,544,204 | B2 * | 6/2009 | Krespi | A61N 5/0603 128/898 |
| 7,789,661 | B2 | 9/2010 | Ostler et al. | |
| 8,371,848 | B2 * | 2/2013 | Okawa | A61B 1/24 433/29 |
| 2004/0076921 | A1 | 4/2004 | Gofman et al. | |
| 2007/0031777 | A1 * | 2/2007 | Wang | A61C 19/004 433/29 |
| 2009/0130622 | A1 * | 5/2009 | Bollinger | A61C 1/0046 433/29 |
| 2010/0047733 | A1 * | 2/2010 | Nahlieli | A61B 1/00167 433/29 |
| 2010/0167226 | A1 * | 7/2010 | Altshuler | A61C 1/0015 433/29 |
| 2014/0065575 | A1 * | 3/2014 | Altshuler | H01S 3/0941 433/215 |
| 2014/0147802 | A1 | 5/2014 | Naldoni | |
| 2014/0272771 | A1 | 9/2014 | Boutoussov et al. | |
| 2014/0316388 | A1 * | 10/2014 | Hipsley | A61F 9/00802 606/4 |
| 2016/0067026 | A1 * | 3/2016 | Esfandiari | A61C 19/004 433/29 |

* cited by examiner

DENTAL LASING DEVICE SYSTEM AND METHOD

PRIORITY CLAIM AND INCORPORATION BY REFERENCE

This application claims the benefit of U.S. Prov. Pat. App. No. 62/631,949 filed Feb. 19, 2018 and entitled Dental Lasing Device System and Method.

This application incorporates by reference, in their entireties and for all purposes, U.S. Pat. No. 9,597,160 entitled LASER-ASSISTED PERIODONTICS and U.S. Pat. No. 5,642,997 entitled LASER EXCISIONAL NEW ATTACHMENT PROCEDURE.

BACKGROUND OF THE INVENTION

Field of Invention

This invention relates to the field of manufactured electrical and manufactured electromechanical devices. More particularly, the present invention relates to medical lasers and to medical lasers using laser diodes.

Discussion of the Related Art

Medical lasers including diode lasers are medical devices such as those defined in 21 U.S.C. 321(h). These devices are manufactured, designed, intended or promoted for in vivo laser irradiation of the human body for purposes including diagnosis, surgery, reconstructive surgery, or therapy.

In dentistry, diode lasers operating at a wavelength of 810 or 980 nanometers (nm) are known while other available wavelengths between 800 and 1064 nm have been used less frequently. Notably, even after U.S. FDA clearance more than 20 years ago, many dentists have little knowledge of lasers.

SUMMARY

The invention described herein relates generally to laser assemblies and to laser assemblies including laser diodes.

FIG. 1 and FIG. 2A-D show a laser assembly 10 and some of the components that may be included therein. In various embodiments, a laser diode module 20 is mounted within a housing 22. The housing may also enclose a laser power meter 70, and an electrical circuit board(s) 80 including mounted components such as a microprocessor 50, A/D converter(s) 11, and complementary circuit elements 13. Laser emission power outlets 15, a transducer to transmit audible alerts, and controls 17 may be provided along with delivery systems including one or more of a single optical fiber for delivery 25, a handle 23, and/or a tip 21. Laser emission outputs of up to several Watts and multiple (e.g., three) wavelengths may be provided from a single laser delivery fiber.

The laser assembly or device 10 may produce laser outputs of up to several Watts. This power is provided to the treatment area by a single laser delivery fiber while the laser(s) are operated at multiple wavelengths, three wavelengths, two wavelengths, or one wavelength. For various procedures one laser may be operated, two lasers may be operated simultaneously, or three lasers may be operated simultaneously.

For example, the laser assembly 10 may be specifically suited to dental applications such as heating, curing, tacking, photopolymerization of composite, cutting soft tissue, disinfecting periodontal pockets, hemostatic assistance, adjunctive use in caries detection, tissue retraction for impressions, gingival incisions and excisions, treatment of aphthous ulcers and herpes type 1 lesions.

Some embodiments of the laser device 10 decrease composite curing time, increase photopolymerization rates of the composite, and/or provide for beneficial use of multiple wavelengths (e.g., 1064 nm, 450 nm, 635 nm) including convenient access to multiple polymerizing wavelengths that avoid the need to change from one laser device to another. Notably, wavelengths may be associated with particular characteristics such as 1064/infrared or non-visible, 450 nm/blue, 635 nm/red.

In some embodiments, the laser device aids the clinician in (a) pinpointing, polymerizing a small area of composite while leaving the rest of the composite flexible for routing around the patient's teeth, and (b) polymerizing composite from the opposite side of the tooth (through the tooth) from the delivery fiber. Broader areas may be polymerized in a conventional manner. This work may take place without the need to adjust controls on the user interface. For example, a lower intensity results from increasing the distance between the output surface of the optical fiber and the surface of the composite material which increases the surface area painted by the polymerizing light. This is due to the conical spreading of the light beam which is proportional to the distance of the fiber to composite surface and the angle $\theta$, theta, the value of which is determined by the numerical aperture of the optical fiber ($NA=n \sin \theta$, where NA is the numerical aperture, n is the index of refraction of the optical fiber, and $\theta$ is the limiting angle of the conically spreading light beam).

In an embodiment, a laser device 10 has a high-power diode laser module 20. The module may produce laser emissions of several Watts power (e.g., 1-6 and up to 25 Watts) via a single optical fiber. The laser emissions outputs 15 may be produced at various visible light wavelengths and at wavelengths above and below those of visible light. For example, wavelengths may include 1064±10 nm, 450±110 nm, and 635±15 nm and the laser emission may be continuous or pulsed.

FIG. 3A-D show laser operating modes 300A-D. When the laser device 10 is programmed for multiple wavelength output or when multiple wavelengths are requested by the operator, laser operation results in a multi-wavelength emission. Emission of these wavelengths may be (a) as a continuous wave (see FIG. 3A), (b) as a series or sequence of individual waves of similar or different wavelengths (see FIG. 3B), (c) as simultaneous emissions of similar or different wavelengths (see FIG. 3C), or (d) as a combination of these such as an emission of a single wavelength followed by an emission of multiple wavelengths followed by an emission of a single wavelength (see FIG. 3D). Any combination of the above emissions may be used. Emissions as in (b) or (d) can occur either in immediate succession or with an overlap such that there are periods of simultaneous emission of two or three wavelengths and at other times there are periods of a single wavelength emission.

The energy emitted from the laser diode module 20 can be pulsed or continuous wave output. For example, the above emissions 3A-D may be pulsed or not and pulse duty cycles may be varied, for example, to control energy delivered. Pulse duty cycles may range from 0.3% to 99% with 100% being continuous operation.

As indicated above, the combinations of multiple, such as two or three, wavelengths may be emitted simultaneously, consecutively, sequentially, or in any order. Sequential emissions may be directed in an overlapping manner, for example where there are intervals during the duty cycle with as many as three simultaneous wavelengths emitted and other intervals where only a single wavelength is emitted. Sequentially means the beginning of a first event falls after the beginning of a second event. Consecutive means following immediately thereafter.

FIG. 4 shows an optical fiber 400. The power of the emissions may be independently measured by an included power meter 70. For example, the power meter may be mounted/configured, for example in a diode lasing device housing, to measure laser power output using a feedback loop for ensuring that actual laser energy delivered corresponds to a selected set point. Notably, the power meter may measure power at various stages of the output, for example at the laser diode module 20, optical bench 533, delivery fiber input 451, or delivery fiber output/probe output 463.

With regard to optical fiber construction, the fiber may have a core diameter 457, for example a 360 μm diameter, and it is from such a diameter that light is emitted, said diameter excluding any coatings or shields that may be required for the proper use or operation of the fiber. In general, core diameters may range between 100 and 1,000 μm and may have numerical apertures (N.A.) within a range of 0.12 to 0.53 with a preferred embodiment range of 0.22 to 0.34.

As discussed, light may be emitted at various wavelengths and emitted using continuous, consecutive, sequential, overlapping sequential, simultaneous, and/or mixed laser operation including pulsed laser operation. This light reaches a delivery fiber 25. The output (distal) end of the fiber may be contained and directed by a hand tool or the light may thereafter reach a hand tool or probe 23 with or without a tip 21 for use on a patient. The delivery chain and its individual components may be optimized to heat and/or polymerize dental composites whether they be inside or outside a tooth. For example, composites may be exposed and thus able to be heated directly. For example, composites may be contained within a tooth or container in which case they may be heated indirectly via a tooth or container wall or sidewall, or the composite may be located on the side of the tooth away from where the output of the delivery fiber may be conveniently presented, and the composite may be heated and cured through the tooth.

The energy is emitted in various patterns, e.g., in a consecutive or sequential pattern (e.g. Near-Infrared followed by Blue) or in a simultaneous pattern (e.g., Near-Infrared and Blue together) or in an overlapping pattern (e.g., Near-Infrared, Near-Infrared and Blue, Blue) so as to heat and polymerize the dental composite.

Other user interface selections adapt the laser device for performing other applications. For example, light energy emitted in the various wavelengths and output in the various patterns/combinations may be conducted by the delivery fiber 25 and used/optimized for hemostatic assistance, adjunctive use in caries detection, tissue retraction for impressions, gingival incisions and excisions, aphthous ulcer treatment, and treatment of herpes type 1 lesions.

Light emissions used for these other applications may be emitted in various patterns. For example, light emissions may include: sequential emissions (e.g., Near-Infrared followed by Blue) or simultaneous emissions (e.g., Near-Infrared and Blue together) or overlapping emissions (e.g., Near-Infrared, Near-Infrared and Blue, Blue) in an effort to assist the operator in performing these procedures.

In an embodiment, a diode lasing device for dentistry and oral surgery comprises: a laser diode module in a lasing device housing; the laser module including three or more laser diodes; a first laser diode (blue) for emitting light with a wavelength of 400 to 510 nanometers at a power of 0.1 to 5 Watts; a second laser diode (infrared) for emitting light with a wavelength of 800 to 1200 nanometers at a power of 0.1 to 25 Watts; a third laser diode (red) for emitting light with a wavelength of 600 to 750 nm at a power of 1 to 1,000 milliWatts; light from the first, second, and third laser diodes received by an optical element for combining multiple laser beams into a single beam; and, a single optical fiber with a core diameter of 100 to 1,000 μm for receiving the single beam and transporting the single beam for use in patient treatment.

The diode lasing device may comprise: an operating mode that varies laser power by pulsing the laser at a frequency of 10 Hz to 50 Hz using 20 to 100 msec pulse width and a 50% duty cycle. The diode lasing device may comprise: another continuous wave operating mode. The diode lasing device may comprise: a first laser operating mode that varies laser power by pulsing the laser at a frequency of 10 Hz to 50 Hz using 20 to 100 msec pulse width and a 50% duty cycle. The diode lasing device may comprise: a second laser operating in continuous wave mode. The diode lasing device may comprise: in the first laser operating mode, the laser duty cycle is 20% to 65%. The diode lasing device may comprise: an output power of the single beam is independently measured and controlled to a particular set point via a feedback loop with a power meter. The diode lasing device may comprise: a facility that sums and displays the accumulated energy output, or light dose delivered, in Joules, beginning at zero and summing during all laser emission periods where the counter may be reset to zero upon operator command. The diode lasing device may comprise: within the diode lasing device housing, a laser power meter that measures actual power (Watts) to confirm the power of the single beam emitted from the fiber equals the displayed power setting. The diode lasing device may comprise: a facility giving timed warnings to prevent a) over-polymerization of a composite or b) over-energizing a tissue. The diode lasing device may comprise: a first laser for emitting light with a wavelength of 400 to 510 nanometers at a power of 0.1 to 5 Watts; and, a laser variable power operating mode that uses pulses at a frequency of 10 Hz to 50 kHz using a 20 to 100 msec pulse.

The diode lasing device may comprise: for in vivo dental composite heating and subsequent photopolymerization, a near-infrared laser operated at 0.4 to 2.0 Watts for 5 to 30 seconds is used to heat the composite for, the laser emitting light with a wavelength of 800 to 1200 nanometers; and, after heating the composite, automatically deactivating the near-infrared laser and automatically activating the blue laser at 0.2 to 0.4 Watts for 1 to 10 seconds using a 10 to 30 Hz pulsed emission for photopolymerizing the composite. The diode lasing device may comprise: for gingival incisions and excisions, the first laser is activated to deliver 0.4 to 1.0 Watts at the distal end of the single optical fiber which is placed proximate the soft tissue to be incised or excised; and, a second laser with a wavelength of 800 to 1200 nanometers for soft tissue incisions and excisions is activated to deliver 0.4 to 1.6 Watts at the distal end of the single optical fiber which is placed in contact with the soft tissue to be incised or excised. The diode lasing system may comprise: for tissue retraction for impression, the first laser delivers 0.4 to 1.0 Watt at distal end of the single optical fiber which is placed in contact with the inner epithelial lining of the free gingival margin, and the tip being angled toward the soft tissue; and, a second laser with a wavelength of 800 to 1200 nanometers for soft tissue retraction delivers 0.4 to 1.0 Watt, the distal end of the single optical fiber placed in contact with the soft tissue to be retracted. The diode lasing system may comprise: for hemostatic assistance, the first laser delivers 0.5 to 1.0 Watt to control bleeding, the distal end of the single fiber 1 to 4 mm away from wounded soft tissue; and, for hemostatic assistance, a second laser with a wavelength of 800 to 1200 nanometers, the second laser delivers 1.0 to 2.0 Watts to control bleeding, the distal end of the single fiber placed in contact with the target tissue. The diode lasing system may comprise: for aphthous ulcer treatment, the first laser delivers 0.4 to 0.6 during a 10 to 30 Hz pulsed emission, the distal end of the single fiber held angled perpendicular to a lesion at a designated distance from the surface; the fiber is moved in a circular motion over the entire lesion and slightly beyond the borders of the ulcer, the circular motions lasting 20 to 40 seconds and repeated 3 to 5 times with 10 to 15 second intervals therebetween; and, a second laser with a wavelength of 800 to 1200 nanometers is for aphthous ulcer treatment, the second laser delivering 0.6 to 1.0 Watt continuous or pulsed emission at 10 to 30 Hz from the distal end of the single fiber which is placed and angled perpendicular to the lesion.

The diode lasing system may comprise: for adjunctive use in caries detection, a blue laser with a 0.1 to 0.3 Watt emission at the distal end of the single fiber is placed in contact with a tooth surface; illumination on the opposite tooth surface is observed; the above steps are repeated to cover substantially the whole surface of the tooth and to examine the entire clinical crown; under laser illumination a) areas of decalcification, superficial stain, and decay that appear darker than healthy enamel are observed, b) the presence of a characteristic luminescence indicative of carious dentin is observed; c) the removal of decay during cavity preparation is observed; and d) through conventional means, the presence of decay is observed.

In some embodiments an appliance for dental and oral surgery uses one or more diode lasers comprising: a laser system with means for outputting a single beam from a laser; the beam having two or more selected wavelengths of light; and, the beam having a pulsed duty cycle. In some embodiments an appliance for dental and oral surgery comprises: laser diode integrated circuits for each wavelength mounted within a module having laser outputs focused by a set of optical elements such that a combined emission is transported by a single optical fiber. In some embodiments an appliance for dental and oral surgery uses one or more diode lasers comprising: the use of selected wavelengths of light, each one of blue with a wavelength of 400 to 510 nm, infrared with a wavelength of 1054 to 1074 and red visible. In some embodiments an appliance for dental and oral surgery uses one or more diode lasers comprises: means for delivering laser power of up to 5 Watts (W) at 450 nm and 10 W at 1064 nm, and up to 1,000 mW at 650 nm.

In some embodiments an appliance for dental and oral surgery uses one or more diode lasers wherein light at each of the wavelengths is emitted at a duty cycle between 20 and 65%. In some embodiments an appliance for dental and oral surgery uses one or more diode lasers wherein the wavelengths are emitted simultaneously. In some embodiments an appliance for dental and oral surgery uses one or more diode lasers wherein the wavelengths are emitted consecutively. In some embodiments an appliance for dental and oral surgery uses one or more diode lasers wherein emissions start at different times but overlap.

Embodiments also include a laser system wherein the emissions alternate with no gap in time therebetween. Embodiments also include a laser system wherein: the beam is delivered by a single fiber with a core diameter within a range of from 100 to 1,000 μm. Embodiments also include a laser system wherein the single optical fiber has a numerical aperture within a range of from 0.12 to 0.32. Embodiments also include a laser system wherein the single optical fiber has a numerical aperture within a range of from 0.18 to 0.28. Embodiments also include a laser system wherein emissions of blue light and infrared light are optimized to heat and photopolymerize in situ dental composite.

Embodiments also include a laser system wherein photopolymerization of dental composites is carried out by positioning a distal end of the laser optical fiber perpendicular to the resin-based composite (RBC) within 2 to 6 mm of the RBC on/within tooth. Embodiments also include a laser system wherein light is delivered in 3-5, 1-6, 4-8, 8-20 second duration cure cycles, with user-commanded timing intervals. Embodiments also include a laser system wherein the optical fiber has cladding and an inside diameter of the cladding is about 360 microns. Embodiments also include a laser system wherein: a Peltier cell is operated as a thermoelectric cooler for cooling the laser module; and, the Peltier cell is between the packaged laser diode module and a heat sink for dissipating the heat lost from the laser module. Embodiments also include a laser system wherein: a motorized cooling fan cools the heat sink; and, the cooling fan is mounted opposite the Peltier cell with the heat sink therebetween.

BRIEF DESCRIPTION OF THE DRAWINGS

The present invention is described with reference to the accompanying figures. These figures, incorporated herein and forming part of the specification, illustrate embodiments of the invention and, together with the description, further serve to explain its principles enabling a person skilled in the relevant art to make and use the invention.

DETAILED DESCRIPTION

Figure 1:
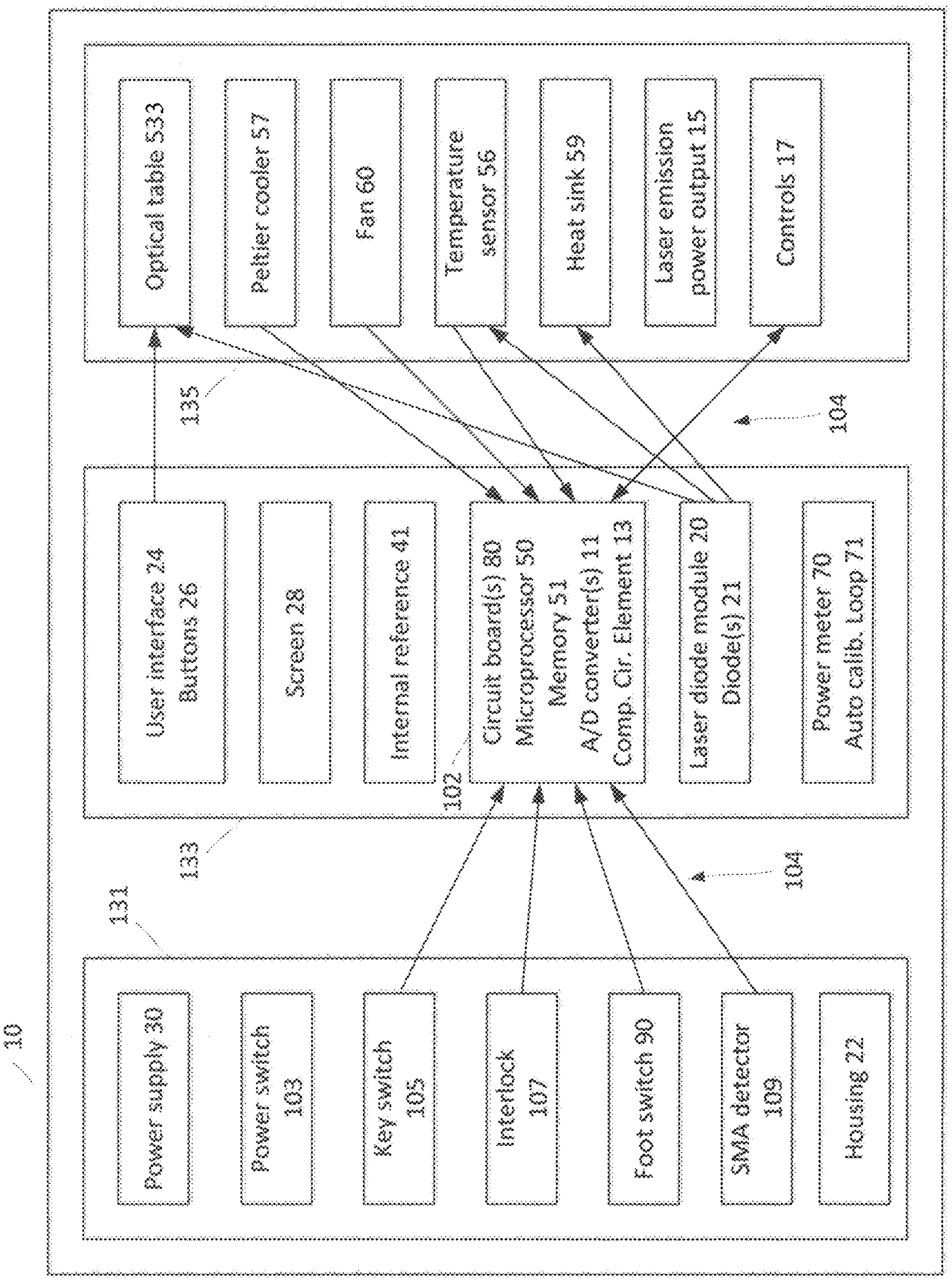
FIG. 1 shows a block diagram of the laser device of the present invention.
Figure 2A:
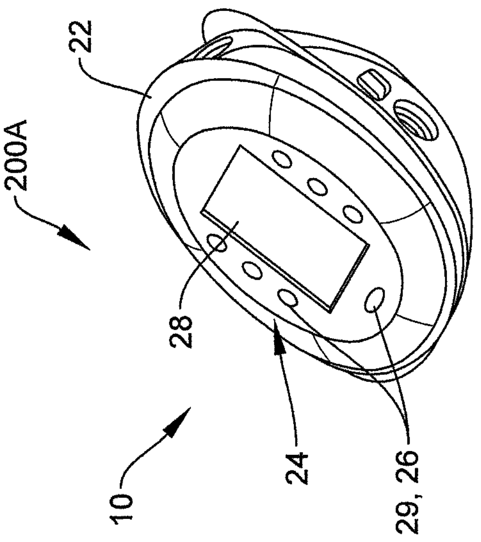
FIG. 2A shows a front elevation view of the laser device of FIG. 1.
Figure 2B:
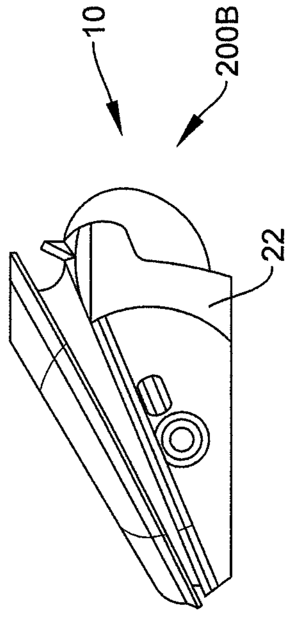
FIG. 2B shows a right side elevation view of the laser device of FIG. 1.
Figure 2C:
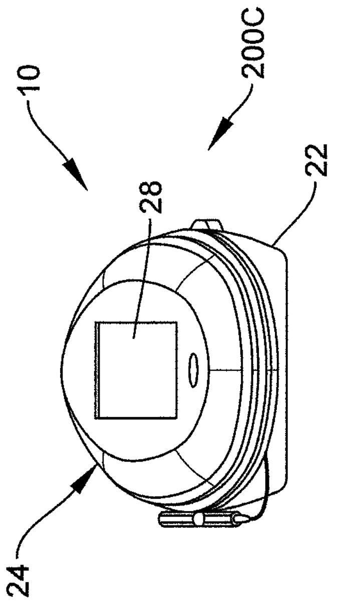
FIG. 2C shows a side elevation view of the laser device of FIG. 1.
Figure 2D:
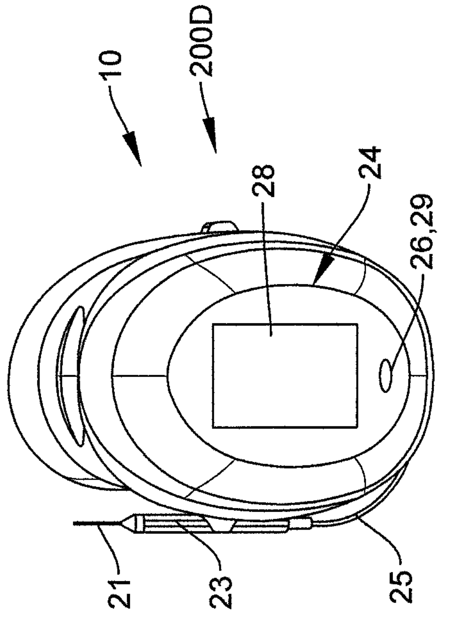
FIG. 2D shows a top plan view of the laser device of FIG. 1.
Figure 3A:
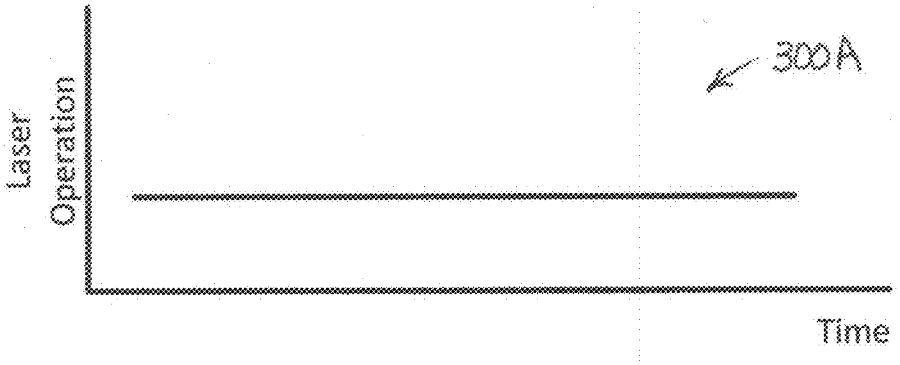
FIG. 3A-D show operating modes of the laser device of FIG. 1
Figure 3B:
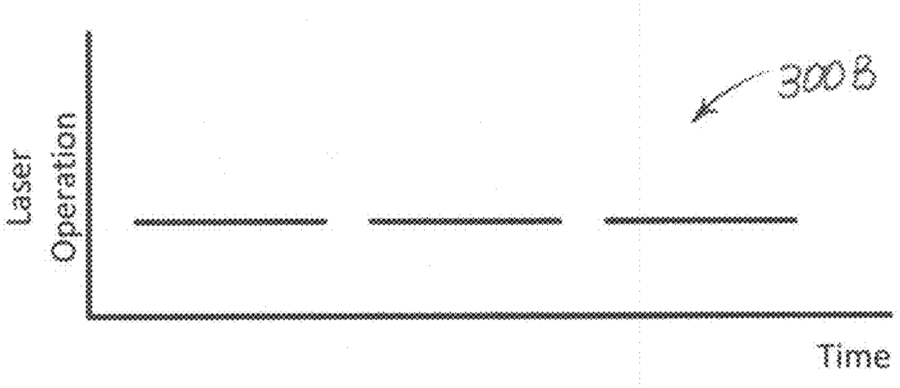
Figure 3C:
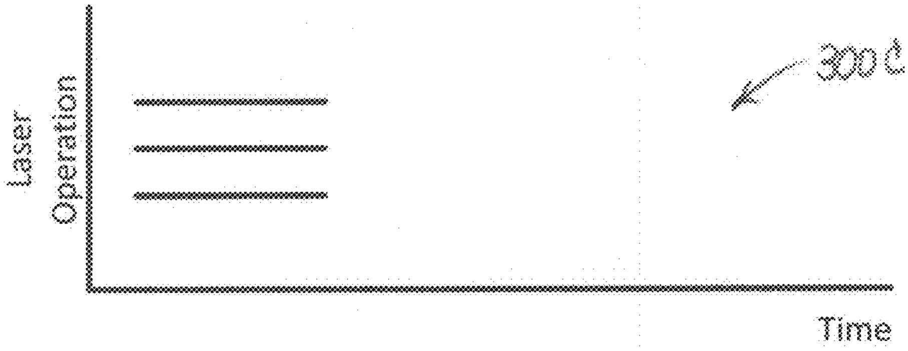
Figure 3D:
Figure 4:
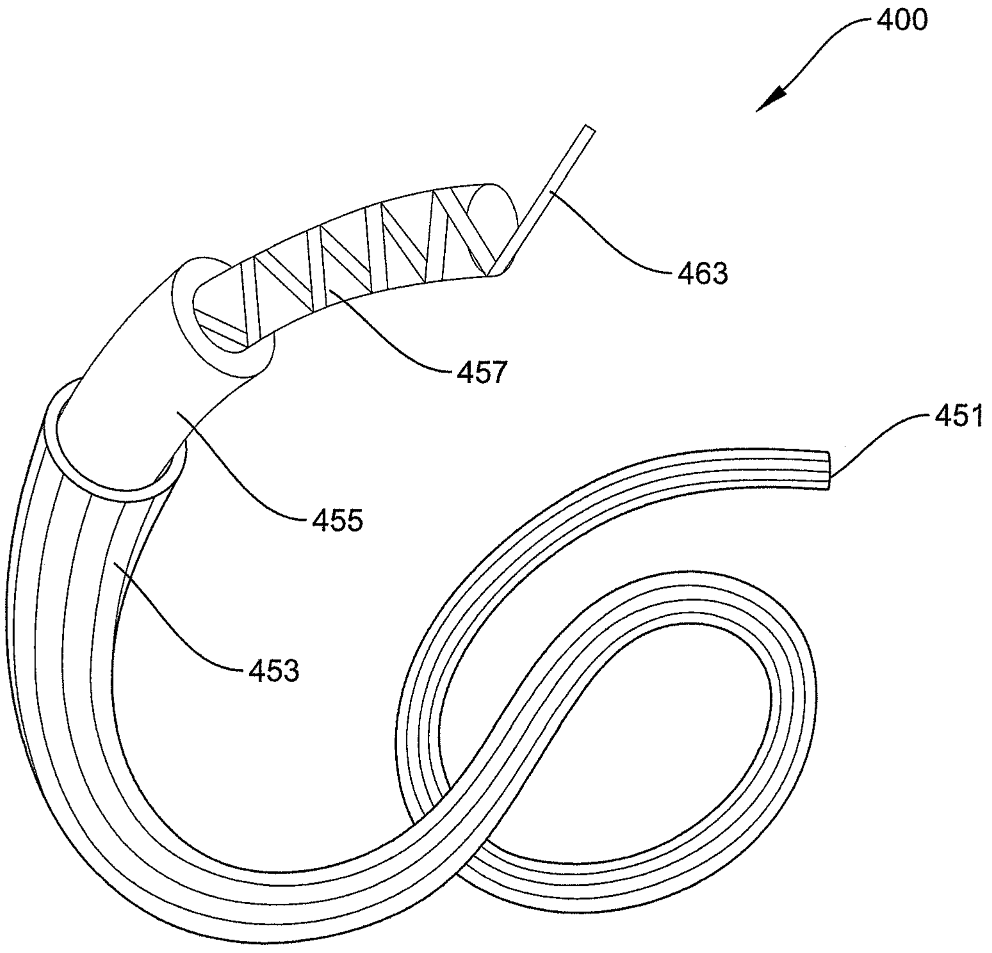
FIG. 4 shows an optical fiber for use with the laser device of FIG. 1.
Figure 5:
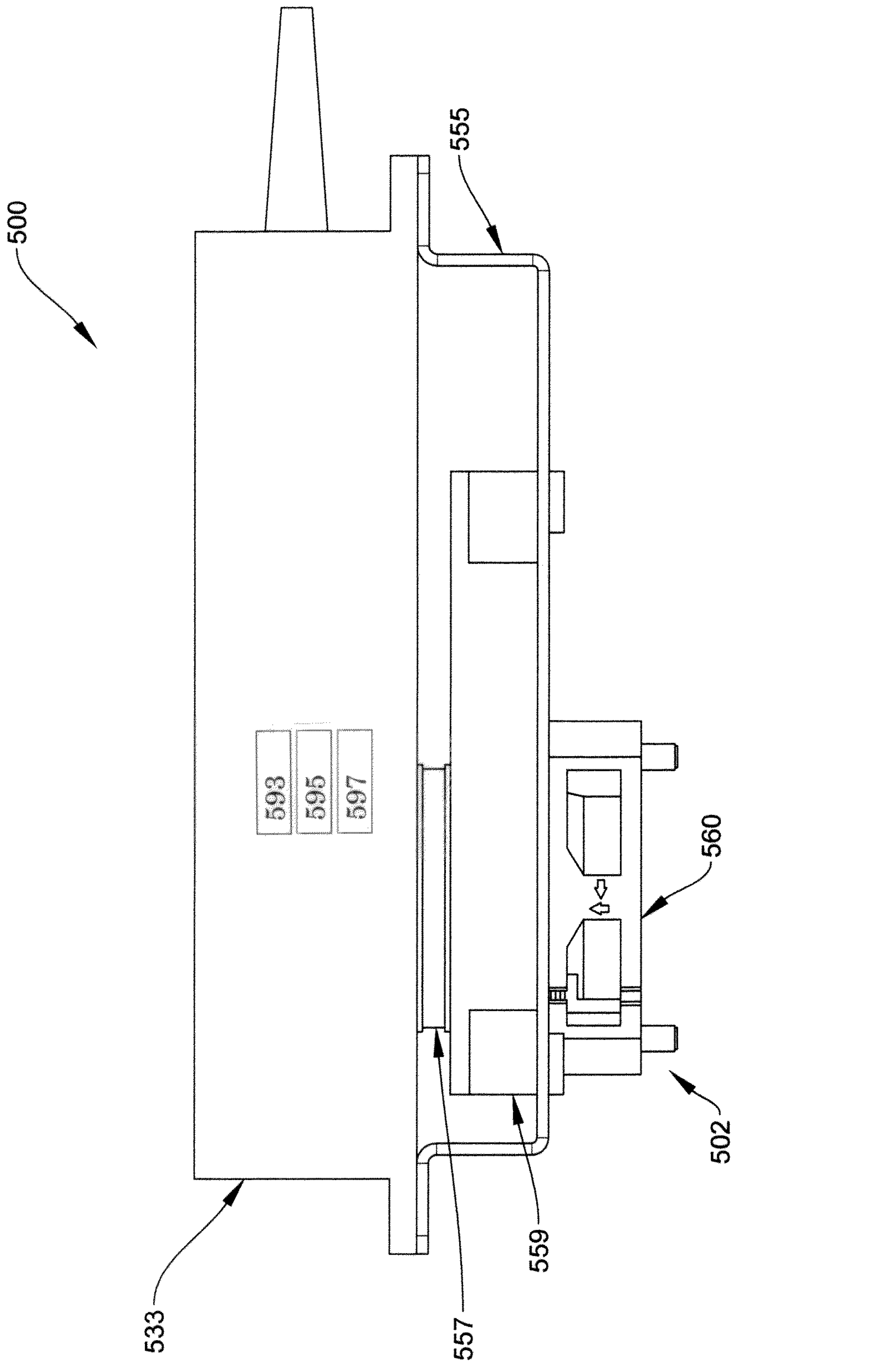
FIG. 5 shows a side view of a cooling system for use with the laser device of FIG. 1.

This disclosure provides examples of some embodiments of the invention. The designs, figures, and description are non-limiting examples of certain embodiments of the invention. For example, other embodiments of the disclosed device may or may not include the features described herein. Moreover, disclosed advantages and benefits may apply to only certain embodiments of the invention and should not be used to limit the disclosed invention.

To the extent parts, components and functions of the described invention transport light, transport signals, or exchange fluids, the associated interconnections and couplings may be direct or indirect unless explicitly described as being limited to one or the other. Notably, indirectly connected parts, components, and functions may be coupled although they have interposed devices and/or functions.

Described herein are embodiments of a dental laser device and methods of performing particular dental procedures using a diode laser device or system. Notably, safe and appropriate use of lasers requires a clinician whose training includes knowledge of laser delivery systems and laser-tissue interactions.

Diode lasers used in dentistry may provide a number of advantages including a bloodless operating field, minimal swelling and scarring, and less or no post-surgical pain. The light produced by these lasers includes wavelengths that may be visible to the human eye and wavelengths that may be above (infrared) or below (ultraviolet) the range of visibility to the human eye.

Lasers emit a coherent wavelength of electromagnetic radiation that may be used to: heat and/or cure dental materials including composites; and cut, coagulate, ablate, or treat tissue in various clinical applications. As mentioned above, laser systems can produce light at different wavelengths and may vary laser power/laser energy levels using, for example, pulses and variable pulse durations.

The coherent light is emitted in various wavelengths and the output may include various combinations of emitted wavelengths. Where laser output is delivered, for example, via optical fiber 25, it may be used to: (a) heat and/or cure and/or polymerize dental composite; (b) heat and then polymerize dental composite; (c) perform hemostatic assistance; (d) retract tissue for impressions, perform gingival incisions and excisions, treat aphthous ulcers and herpes type 1 lesions; (e) provide adjunctive use in caries detection; and (f) perform photocoagulation or vaporization of soft or fibrous tissue, curing of light-activated dental materials, adjunctive use for endodontic orifice location, and light-activation of bleaching materials for teeth whitening.

In various embodiments the laser device 10 of the present invention may include a logic section 133, a first accessories section 131, and a second accessories section 135. The first accessories section includes one or more of a power supply 30, a power switch 103, a key switch 105, an interlock 107, a foot switch 90, SMA device(s), a transducer for transmitting audible alerts, and a housing 22. SMA devices may include SMA connector(s) and/or SMA detector(s) 109, the detectors for detecting proper optical and/or mechanical interface(s).

The logic section includes one or more of a user interface 24, buttons 26, screen 28, internal reference 41, circuit board(s) 80, microprocessor 50, memory 51, A/D converter(s) 11, complementary circuit element 13, laser diode module 20, laser diodes 21, a power meter 70, and an auto calibration loop 71.

The second accessories section includes one or more of a wavelength combiner or optical table 533, Peltier cooler 557, fan 60, temperature sensor(s) 56, heat sink 59, laser emission power output 15, and controls 17. Details concerning a number of these components are provided below.

Laser Diode Module

The laser diode module 20 includes laser diode semiconductor device(s) and circuitry that supports the laser diodes. In various embodiments the dental lasing device includes a housing 22, one or more electrical circuit boards 80, a microprocessor 50 mounted on one of the circuit boards, an optical table 533, and interconnecting conductors 104.

Each diode 21 of the laser diode module 20 is a coherent light source where coherent light refers to an emission of light at a single frequency and phase. For example, the light emission may be in the visible, near-infrared ("IR"), or infrared spectrum. The coherent light may be provided at multiple wavelengths and at variable/high power 25.

Each of the wavelength-specific laser diode integrated circuits ("ICs") is mounted within the laser diode module 20. The laser outputs of the ICs are directed to an optical table 533 that includes a set of optical elements 54 focusing light at various wavelengths into a single optical fiber 25. Electrical current passing through the semiconductor 21 PN or NP junction stimulates and regulates the energy production of a coherent light emission. In a similar manner, when the electrical current stops so too the emission stops.

In an embodiment, the laser diode module 20 includes three diode sub-modules 21. Each sub-assembly produces an emission at a particular wavelength or wavelength band. Exemplary wavelengths or wavelength bands include 1064±10 nanometers (nm) wavelength, 450±10 nm wavelength, and 635±15 nm wavelength.

Diode capacity may be selected to provide various power outputs. For example, the maximum power of the 450 nm emission band may be 5 Watts (W), the maximum power of the 1064 nm emission band may be 25 W, and the maximum power of the 635 nm band may be 1,000 mW (milliWatts).

As shown above, in some embodiments the laser diode module 20 includes laser diodes 21 whose center wavelength varies from values of 450, 635 and 1064 nm. For example, the 450 nm laser diode may be replaced/augmented with a laser diode having a center wavelength 450 nm±4.5 to 45 nm (e.g., 1% to 10%). In a similar manner the 635 and 1064 nm diodes may be replaced/augmented.

And, in some embodiments, light from diodes 21 that provide a broader spectrum is filtered by opto-mechanical assemblies included in the light table. Notably, various ones of these broad spectrum diodes may require additional cooling using Peltier cell cooling 57, water cooling, or another suitable cooling means known to persons of ordinary skill in the art.

Optical Table

In various embodiments, the laser diode module 20 may combine laser emissions of various wavelengths. The module may include plural optical fibers attached to plural diodes 21. Diode or fiber optical outputs may be combined via one or more opto-mechanical devices 533 such that a single output for use with a single optical fiber results.

In another embodiment beams are combined. Here, multiple distinct beams from multiple lasers impinge on a transformation lens which focuses the beams to a single point on a dispersion element. The dispersion element emits a single beam that impinges on an external cavity mirror. In combination, the external cavity mirror and dispersion element may define an external cavity. Notably, the dispersion element may turn the emitted beam through an angle of 90 degrees relative to the beams emitted by the lasers.

In another embodiment beams are combined. Here, multiple distinct beams from multiple lasers impinge on a transformation lens 593 which focuses the beams to a single point on a dispersion element 595. The dispersion element emits a single beam that impinges on an external cavity mirror 597. In combination, the external cavity mirror and dispersion element may define an external cavity. Notably, the dispersion element may turn the emitted beam through an angle of 90 degrees relative to the beams emitted by the lasers.

Optical Fiber Delivery

An optical delivery fiber 25 is attached to the laser diode module 20. In various embodiments the attachment is via a single mechanical and optical interface located at the optical table output 15.

As mentioned, the optical delivery fiber core 457 from which light is emitted has a diameter of between 100 and 1000 μm. The fiber has a numerical aperture (N.A.) within a range of about 0.12 to 0.53 and a preferred embodiment in the range of about 0.22 to 0.34. The core may be sized to deliver laser power of up to 5 W at 450 nm, 25 W at 1064 nm, and up to 1,000 mW at 635 nm. The distal end of the optical delivery fiber 25 may be attached to a hand-held probe 23 useful for directing the fiber output.

System Cooling

Semiconductors and opto-mechanical devices have thermal losses. For example, not all of the electrical current passing through the laser diodes is converted into coherent light emissions.

This efficiency loss includes junction resistance where the heat generated is proportional to the product of the semiconductor junction resistance and the current to the second power (I^2*R). In similar fashion, where the emission is reflected and transmitted within the opto-mechanical components 54 thermal losses occur.

Thermal losses tend to cause a temperature rise in the laser diode module 20. But, the module 20 must be maintained within a suitable temperature range (e.g., 50 to 80 degrees Celsius) that avoids IC thermal damage or degraded performance.

A cooling system 502 solves this problem for the above-mentioned laser diode module 20. The cooling system includes temperature sensor(s) 56, a cooling module 557, heat sink(s) 559, and a fan 560. In various embodiments, the cooling module is a Peltier cell tune thermo-electric cooler.

The cooling system 502 is mounted near to or to the optical table 533 and a cooling system bracket 555 may be used to fix the cooler. The cooling system or its bracket includes temperature sensors 56 providing feedback for controlling operation of the thermo-electric cooler 557. Heat transferred to the heat sinks from the thermo-electric coolers is subsequently removed from the heat sinks by circulating air provided by the cooling fan 560 such as a muffin fan.

In some embodiments, the cooling system 502 cools the wavelength combiner or optical table 533 and/or the diode module 20. For example, the diode module may be within the optical table or it may be cooled separate from the optical table.

In some embodiments, the lasing device of claim includes a Peltier cell operated as a thermoelectric cooler for cooling the laser module and the Peltier cell is located between the packaged laser diode module and a heat sink for dissipating the heat lost from the laser module. And in some embodiments a motorized cooling fan cools the heat sink and the cooling fan mounted opposite the Peltier cell with the heat sink therebetween.

Current Control

In the laser diode module 20 electrical current passes through the laser diodes in response to microprocessor controls. The electrical current transferred to the diodes 21 is in response to commands that include analog and/or digital signals. For example, digital commands from the microprocessor may subsequently be converted to analog signals before they are used to control the laser diodes.

The energy emitted from the laser diode module can be varied. For example, the laser may be turned off and on repeatedly and/or rapidly such that the laser emission "pulses." In this case, a pulse duty cycle controls the energy delivered by the laser. These pulses may provide various wavelengths of light that are in time arranged in parallel or serially. In cases the pulses of light may overlap.

In another case, the laser device 10 is operated continuously such that the laser power output may be at levels indicated by the laser output power rating. Whatever the case, the laser power level is determined by a microprocessor command or instruction that sets the laser power level.

Laser diode module 20 including multiple laser diodes 21 have emissions that can include several wavelengths of light, for example the discrete wavelengths emitted may be as numerous as the laser diodes. These diodes may be operated to emit wavelengths one at a time or in some or any combination.

For example, the combinations of two or three wavelengths may be emitted simultaneously, in sequence, or in any order selected by the laser operator. Sequential emissions may be directed in an overlapping manner where, for example, there are intervals during the duty cycle when two or more, or three, wavelengths are emitted simultaneously and other intervals where only a single wavelength is emitted.

As discussed above, this emission of one or more wavelengths may be carried by a single fiber. In various embodiments this single fiber is connected to the laser diode module or to the optical table output.

For pulsed lasers, the duty cycle may be from 0.3% to 99% with 100% being continuous duty. Where the lasers emit 5 W at 450 nm, 25 W at 1064 nm, and 1000 mW at 635 nm, clinically effective duty cycles may vary in the range from about 20% to about 65%.

Preferred Operating Specifications

Operating modes may include continuous wave (CW) operation, pulsed operation, and pulsed operation at 25 Hz. Operating modes may also include serial pulsed mode where, for example, 20 seconds of operation at 1064 nm is followed by 5 seconds of operation at 450 nm and thereafter, simultaneous pulsed mode operation at 1064 nm and 450 nm.

Output power for the 1064 nm wavelength may be 0.5-25 Watts in CW mode (0.1 W increments) and 0.1 to 25 Watts average in pulsed mode. In serial pulsed mode up to 2 Watts average power may be used. In simultaneous pulsed mode, the power may be 0.1-2 Watts total average power which is the sum of the power from the 1064 nm beam and the power from the 450 nm beam where these beams are of equal power.

Output power for the 450 nm wavelength may be 0.1 to 5 Watt in CW mode and 0.1 to 2 Watts average power in pulsed mode. In serial pulsed mode up to 2 Watts average power may be used. In simultaneous pulsed mode 0.1-2 Watts total average power (50%/50%) may be used.

Output power for the 635 nm wavelength may be 1000 mW maximum with an aimed beam. In pulsed mode the pulse width may vary from 10 nanoseconds to 500 milliseconds.

In some embodiments, input power of a three diode laser device is 30 Watts. And in some embodiments, the related input voltage is 12 Volts DC.

Internal Power Meter/Auto Calibration Loop

Factors such as optical fiber contamination, radiation fatigue, and improper output fiber cleaning may affect or negatively affect laser output power. Power meter 70 enables measuring laser power output.

The power meter 70 is mounted for measuring laser power output. For example, power output may be measured at the laser diode module 20, at the wavelength combiner or optical table output 15, or at the distal end of an optical fiber (delivery fiber) connected to the output 15. This power meter enables calibration of the laser power output such that at a particular indicated laser power (e.g., laser power setting) the laser delivers a specific or predetermined amount of power.

In an embodiment this is accomplished by using a laser device 10 internal reference 41 to which the power meter 70 reading is compared. In various embodiments, auto calibration is provided using the power meter and the internal reference. In some embodiments, where laser output is measured at the output 15, auto calibration takes into account losses that occur in the delivery fiber 25 and may take into account losses that occur in any optical fiber attachments 21. In such cases, this may provide more accurate estimates of energy delivered to the treatment site.

In some embodiments, a calibration subsystem 71 is used for diode lasing device calibration. Here, diode lasing device displayed power setting is set to deliver a specific power that matches an internal power reference 41. When the power meter 70 measures the actual laser power exiting the delivery fiber 25, this measurement should match the reference power value. If it does not, the displayed power setting is adjusted to read a power equal to that of the internal power reference 41. This restores the laser to a calibrated state.

In some embodiments a diode lasing device calibration subsystem 71 measures laser power exiting the delivery fiber 25, makes a comparison with a reference power 41 and uses a feedback loop to adjust the current passing through the Laser Diode(s). In this manner, the actual power is made to converge with user-requested values. As a safeguard, this feature may ensure actual laser power delivered to the treatment site corresponds to a desired output setting made via the user interface.

The power meter may use detection sensors in measuring the energy of the coherent light emissions such as emissions exiting the delivery fiber. Here, the power meter is an analog emission sensor whose output is converted from an analog value to a digital value in an Analog to Digital (A/D) conversion.

Power meter 70 digital readings provide suitable accuracy and throughput which enables a microcontroller to make a timed or time-phased energy measurement. This measurement of fiber emission is converted into an average power value and a comparison is made. For example, the comparison may be with a reference average power value as mentioned above. Thereafter, the microprocessor/microcontroller 50 issues a digital command which becomes an analog control signal presented to the laser diode module 20 to adjust the current flowing through the laser diodes 21. The output of the laser device 10 is adjusted as the current flow through the diodes is adjusted.

Error messages and/or a halt to laser device 10 operation occur when the microcontroller senses an error or unsafe condition or an error or unsafe condition that cannot be corrected. For example, the microcontroller may issue an error message and temporarily halt laser operation when a correction command exceeds safety envelopes dictated by optical and electrical capacities of the laser device. The microprocessor may issue audible alerts transmitted via the transducer to notify the operator that laser operation has been temporarily halted or to draw attention to critical time periods which have elapsed warning that there is a potential for overpolymerization during the curing cycle, e.g., 3 and 5 second time markers, or to advise that laser light dosimetry is nearing the maximum recommended therapeutic levels or advise of the potential for overenergizing the target substance or tissue.

The output power is measured and displayed with precision by a function that measures, sums and displays the accumulated energy output, or light dose delivered, in Joules, by the system during a specified time period. The user interface records the beginning time period from which the Joules of light emission energy are recorded. The energy is summed (accumulated) and displayed as the total Joules emitted from the beginning time until present.

User Interface Housing

A diode lasing device or user interface housing 22 may include a front-mounted user interface 24. In a first embodiment, interface 24 may use tactile keypad buttons 26 providing for entry of fixed commands into a system microprocessor 50. These commands are interpreted as input and command parameters by firmware resident in the microprocessor module. Results and responses are displayed on a screen 28 and may be indicated by lamps 29. For example, light-emitting diode(s) (LEDs) may be within keypad buttons 26. While this embodiment 10 can be implemented without difficulty, it may suffer from providing too little information to a user. However, it is expected that an experienced laser technician will be able to operate this first embodiment without difficulty.

In another embodiment, interface 24 screen 28 may be a touch-sensitive display allowing entry of commands without requiring mechanical switches.

In another embodiment, interface 24 may comprise a single keypad (not shown) with a screen 28 or screen capable of color display such as organic light-emitting diode(s) ("OLEDs") with capacitive 15 touch-screen overlays or other moderate-to-high-resolution touch-sensitive displays such as those used for cellular telephones and other devices requiring touch screen command and display capabilities.

The display 28 may be within keypad buttons 26 or centered within keypad buttons 26 as shown in FIG. 1. And, keypad buttons 26 may be used to enter fixed commands into microprocessor 50 with results displayed in detail on screen 28.

In this embodiment, more information may be presented on screen 28 with color functioning to communicate particular aspects of the information such as state or degree. Embodiments above may use fixed commands or not. These I/O ("input/output") devices may include or be a part of subsystems intended to make the laser device immune or resistant to electrical problems including interference, power surges, and stray radio frequency signals.

Laser device 10 activation may be accomplished by various means including any devices that interpret human motion. For example, hand motion, foot motion, eye motion, knee motion, and the like. In some embodiments, the system is activated using foot or hand motion, for example, a foot- or hand-manipulated switch 90.

In an embodiment, an electromechanical actuator, preferably a foot switch 90 is used. The switch may have normally open, single-throw multi-pole contacts and may be located in a housing or mechanical enclosure suitable for operation by the human foot. This foot switch may be used to provide hands-free initiation of lasing and can be either a corded switch or a wireless switch known in the art. A corded foot switch may be used when interfering radio wave emissions are anticipated.

Power Supply

The system includes a power supply 30. Power supply inputs may be 100-240 VAC and power supply outputs may be 12 VDC or 5 VDC at 3 A or 4 A maximum. Power supply 30 may be a commercial supply with 100-240 volts alternating current input and may be able to supply output current at 4 A to circuit board 80 and cooling fan 60. The dental lasing device power supply 30 may provide both 5 and 12 VDC to circuit boards 80 or components requiring these voltages.

The lasing device is compact and portable. Laser diode module 20 may be mounted within a housing 22 such as an injection-molded plastic housing. Housing 22 may have a front-mounted user interface 24 adapted for user operation.

In an embodiment, the housing is plastic and includes Acrylonitrile butadiene styrene (ABS). The laser device 10 may have dimensions of approximately 10.5 inches long, 7.25 inches wide, and 6 inches high. Any of these dimensions may vary by ±25%. The weight of the laser device is approximately 2.5 pounds and the weight may vary by ±25%. See for example FIGS. 2A-2D.

As described, embodiments of the present invention may include a plurality of individual parts. Similarly, methods may include a plurality of individual steps. These descriptions are intended to illustrate and may be augmented by additional parts or steps as indicated for carrying out the functions contemplated herein. Parts and/or steps may be changed, they may also be omitted and the order of the parts or steps may be re-arranged while maintaining the sense and understanding of the device and methods as claimed.

We turn now to particular embodiments of the lasers disclosed herein. Shown in the table below are blue lasers and infrared surgical lasers used in various applications. Red lasers are also included and used, for example, as an aiming beam to make a combined beam visible.

| LASER TYPE | LASER CHARACTERISTICS | Applications |
|---|---|---|
| Blue Laser | Wavelength 400 to 510 nm with a preferred range of 440 to 460 nm and a typical wavelength of 450 nm<br>Power 0.1 to 5.0 Watts with a preferred range of 0.1 to 2.0 watts<br>Emission mode continuous wave or pulsed<br>Pulse frequency 0.1 Hz to 30 kHz with a preferred range of 10 to 50 Hz<br>Pulse width 1 µs to 5 seconds with a preferred range of 20 to 100 msec, with a 50% duty cycle | Photopolymerization<br>Antibacterial<br>Virucidal<br>Incision and excision<br>Hemostasis and coagulation<br>Diagnostic<br>Activate tooth whitening agent |
| Infrared Surgical Laser | Wavelength 800 to 1200 nm with a preferred range of 1054 to 1074 nm and a typical wavelength of 1064 nm<br>Power 0.1 to 25 Watts with a preferred range of 0.1 to 3.0 Watts<br>Emission mode CW or pulsed<br>Pulse Frequency 0.1 Hz to 30 kHz with a preferred range of 10 to 50 Hz<br>Pulse width 1 µs to 60 seconds with a preferred range of 20 to 100 msec, with a 50% duty cycle | Preheating composite<br>Photobiomodulation<br>Antibacterial<br>Incision and excision<br>Hemostasis and coagulation<br>Heat tooth whitening agent |

-continued

| LASER TYPE | LASER CHARACTERISTICS | Applications |
|---|---|---|
| Red Visible Laser | Wavelength 600 to 750 nm with a typical value of 635 nm<br>Power 1 mw to 1.0 W with a typical value of 10 mW<br>Emission mode CW or pulsed with a typical value of CW | Aiming beam<br>Photobiomodulation |

The above blue and infrared lasers may provide CW outputs and pulsed outputs. In various embodiments laser modes include one or more of (a) pulsed individual wavelengths, (b) pulsed consecutive wavelengths, c) sequential wavelengths, and (d) pulsed simultaneous wavelengths.

Duty cycles of the above are in the range of 0.3% to 99% for pulsed variants. Where the duty cycle is 100% the mode is continuous. Optical fiber core diameters for the above lasers range from 100 to 1,000 µm or in the range of from 300 to 400 µm.

Notably, where the treatment beam is not visible, an aiming beam is required. Aiming beams may be in a GOO to 750 nm wavelength range, be provided a power of 1 to 1,000 mW, and be either of a CW or pulsed emission. In its higher power range this emission band can be used for Photobiomodulation.

In various embodiments, photobiomodulation is a form of light therapy that utilizes non-ionizing visible and infrared light in a nonthermal process that results in beneficial therapeutic outcomes including but not limited to the alleviation of pain or inflammation, immunomodulation, and promotion of wound healing and tissue regeneration. Photobiomodulation is also known as biostimulation, an anti-inflammatory treatment using selected wavelengths of light. Biostimulation releases adenosine triphosphate (ATP) from the mitochondria of living cells to improve protein synthesis and upregulates several growth factors.

We turn now to examples of particular procedures that use embodiments of the laser device disclosed herein.

Dental Composite Heating and Photopolymerization: In this procedure, dental composite may be used, for example, to fill a tooth while the composite is pliable and thereafter be cured into a hardened state. This is a new and novel method involving the laser diode device 10 for heating composite in vivo and then polymerizing the composite.

1. The desired composite material is placed into the cavity preparation of a tooth.
2. The appropriate laser safety eyewear is worn by the patient, clinician, and other operatory personnel.
3. An optical fiber is placed into a handpiece.
4. The composite material is approached by the operator with the handpiece and optical fiber to a designated distance from the composite material, e.g., 2 to 20 mm.
5. The near-infrared diode laser is activated at clinically relevant settings, e.g., 0.4 to 2.0 Watts, continuous emission, and used to heat the composite for the desired length of time, e.g. 5 to 30 seconds.
6. The blue laser beam is then activated automatically or independently for photopolymerization (curing) of the composite for designated time periods, e.g. 1 to 10 seconds, and settings, e.g., 0.2 to 0.4 Watts, pulsed emission, 10-30 Hz, as selected by the operator.
7. The near-infrared laser beam can be activated consecutively or simultaneously with the blue laser beam at the operator's discretion.

8. The blue laser beam can be activated according to specific clinical need, e.g., photoactivation of bonding materials, composite cements, composite restorations, endodontic composite cores, prosthetic reline/repair material, sealants, splint material, tack-curing of veneers and crowns.
9. A small "spot" size of designated diameter, e.g. 1 to 6 mm, can be operator-controlled by varying the distance from the fiber tip to the target area, e.g., 2 to 20 mm.
10. Bulk cure can be initiated by increasing the distance from the composite, thus increasing spot size, with appropriate operator-controlled adjustments made to output power to achieve the desired power density for curing.
11. Composite may alternatively be cured through the structure of the tooth enamel from the outside into the tooth cavity preparation.
12. Composite may also be cured through nonmetallic matrix bands (e.g., polyester, celluloid, and acetate) from the outside into the tooth cavity preparation.
13. A ceramic restoration may be cured from the opposite side of the veneer, for example, through tooth structure, to "shrink" the composite toward the tooth.
14. Veneers and crowns may be tack-cured in one or two areas, thereby anchoring the restoration in place and facilitating removal of the uncured composite interproximally prior to final photopolymerization.

Gingival Incisions and Excisions: It is noted that traditional surgical excision is difficult, is a source of post-surgical pain, and invites bacterial colonization. Use of the laser procedures below mitigates these problems.

1. Anesthesia (topical or injection) is administered as needed.
2. The appropriate laser safety eyewear is worn by the patient, clinician, and other operatory personnel.
3. An optical fiber is placed into a handpiece.
4. The blue laser is activated at clinically relevant settings, e.g., 0.4 to 1.0 Watt, and the distal end of the fiber is placed in light contact with the soft tissue to be incised or excised.
5. Alternatively, the fiber may be held slightly out-of-contact with the target tissue, e.g., 1 to 3 mm away.
6. The fiber is moved with a rapid, smooth, stroking motion to vaporize layers of tissue at a time.
7. As needed, cutting efficiency may be improved by keeping the tissue taut.
8. For fibroma removal, the tissue to be removed is grasped with forceps and pulled in a perpendicular manner while lasing.
9. The near-infrared laser may be used singularly or simultaneously with the blue laser for soft tissue incisions and excisions.
10. When used singularly, the near-infrared laser beam is activated at clinically relevant settings e.g., 0.4 to 1.6 Watts, and the distal end of the fiber is placed in light contact with the soft tissue to be incised or excised.
11. As needed to optimize tissue interaction with the near-infrared wavelength, the distal end of the fiber tip may first be initiated by lightly tapping the fiber end on a sheet of articulating paper prior to placing the fiber in light contact with the tissue.
12. When the two laser wavelengths are used simultaneously, the parameters are adjusted to clinically relevant settings, e.g., 0.4 to 1.6 Watts.

Tissue Retraction for Impression: Retractions require management of soft tissue. Traditional soft tissue management includes hemorrhage control while exposing prep margins and this requires additional time. Laser procedures reduce problematic bleeding and soft tissue management time.

1. Anesthesia (topical or injection) is administered as needed.
2. The appropriate laser safety eyewear is worn by the patient, clinician, and other operatory personnel.
3. An optical fiber is placed into a handpiece.
4. The blue laser is activated at clinically relevant settings, e.g., 0.4 to 1.0 Watt, and the distal end of the fiber is placed in light contact with the inner epithelial lining of the free gingival margin, with the tip angled toward the soft tissue.
5. The fiber is moved with a constant, steady, circular motion on the buccal, labial, and lingual surfaces to achieve a full-360-degree trough.
6. The near-infrared laser may be used singularly or simultaneously with the blue laser for soft tissue retraction.
7. When used singularly, the near-infrared laser beam is activated at clinically relevant settings, e.g., 0.4 to 1.0 Watt, with the distal end of the fiber placed and angled as specified above.
8. As needed to optimize tissue interaction with the near-infrared wavelength, the distal end of the fiber tip may first be initiated by lightly tapping the fiber end on a sheet of articulating paper prior to placing the fiber in light contact with the tissue.
9. When the two laser wavelengths are used simultaneously, the parameters are adjusted to clinically relevant settings e.g., 0.4 to 1.0 Watt.

Hemostatic Assistance: Dental surgical procedures frequently require hemostatic agents. Tissue biopsies, placement of endosseous implants, and periodontal surgery are just some examples where hemostatic agents may be beneficial. Frequently there is a need to limit the use of these hemostatic agents. Laser surgery provides a solution because the tools and methods of laser surgery inherently reduce bleeding.

1. Anesthesia (topical or injection) is administered as needed.
2. The appropriate laser safety eyewear is worn by the patient, clinician, and other operatory personnel.
3. An optical fiber with noninitiated tip is placed into a handpiece.
4. The blue laser is activated at clinically relevant settings, e.g., 0.5 to 1.0 Watt, continuous emission, and the distal end of the fiber is held slightly out-of-contact with the targeted soft tissue, e.g., 1 to 4 mm away.
5. The fiber is moved with a constant, sweeping motion over the bleeding area.
6. The near-infrared laser may be used singularly or simultaneously with the blue laser for hemostatic assistance.
7. When used singularly, the near-infrared laser beam is activated at clinically relevant settings, e.g., 1.0 to 2.0 Watts, pulsed or continuous emission, with the distal end of the fiber placed in light contact with the targeted soft tissue and moved as specified above.
8. As needed to optimize tissue interaction with the near-infrared wavelength, the distal end of the fiber tip may first be initiated by lightly tapping the fiber end on a sheet of articulating paper prior to placing the fiber in light contact with the tissue.
9. When the two laser wavelengths are used simultaneously, the parameters are adjusted to clinically relevant settings, e.g., 0.5 to 1.0 Watt.

Adjunctive Use in Caries Detection: Visual diagnosis is the standard of caries diagnosis. Laser fluorescence not only provides for visual detection but laser fluorescence can also be used for monitoring the disease.

1. The appropriate laser safety eyewear is worn by the patient, clinician, and other operatory personnel.
2. An optical fiber with noninitiated tip is placed into a handpiece.
3. The blue laser is activated at clinically relevant settings, e.g., 0.1 to 0.3 Watt, continuous emission.
4. The distal end of the fiber is placed in light contact with a tooth surface and the illumination is observed on the opposite surface. The fiber is redirected over the whole surface to enable examination of the entire clinical crown.
5. Under blue laser illumination, areas of decalcification, superficial stain, and decay appear darker than healthy enamel. Carious dentin exhibits a characteristic luminescence.
6. The presence of decay is confirmed through conventional means.
7. Blue laser illumination may also be used to determine whether all decay has been removed during cavity preparation.

For the above procedures blue lasers may be used with wavelength of 400 to 510 nm, power of 0.1 to 5.0 Watts, emission mode continuous wave or pulsed, and pulse frequency 0.1 Hz to 30 kHz with pulse width 1 μs to 5 sec. For the above procedures, infrared surgical lasers may be used with wavelength of 800 to 1200 nm, power of 0.1 to 25 Watts, emission mode continuous wave or pulsed, and pulse frequency of 0.1 to 30 kHz with pulse width of 1 μs to 60 sec. In various embodiments, aiming beams may be used where the treatment beam is not visible, for example, a 600 to 750 nm wavelength beam may be used with a power of 1 to 1000 mW and the beam may be continuous wave or pulsed. In various embodiments delivery optical fiber core diameter range may be in the range of 100 to 1000 μm. In various embodiments, the duty cycle may be in the range of 0.3% to 99% with 100% continuous wave operation.

We turn now to additional laser setup and laser operation procedures that use embodiments of the laser device disclosed herein. Examples of use of the laser device for dental procedures including photopolymerization of dental composites follow.

| SETUP | LASER OPERATION |
|---|---|
| I. Photopolymerization using simultaneous method of operation Place composite into a tooth. Position laser optical fiber perpendicular to the resin-based composite (RBC) within 2 to 6 mm of the RBC on/within tooth And/or additionally or alternatively position laser optical fiber perpendicular to OPPOSITE side and on/or near tooth 25 structure in order to polymerize THROUGH the tooth and polymerize the RBC from its tooth/RBC contact interface And/or additionally or alternatively position the laser optical fiber to the OPPOSITE side of the restoration or tooth to cure through cement-based material. | Press a foot switch or other activator to simultaneously activate near-infrared and blue wavelengths and simultaneously heat and photopolymerize the RBC. The light is delivered 3-5, 1-6, 4-8, 8-20 second duration cure cycles, with user-selectable timing intervals. Audible alarms are initiated by the microprocessor and transmitted through the transducer to draw attention to critical time periods which have elapsed during the curing cycle, e.g., 3 and 5 second warning periods, or to advise of the potential for overenergizing the target substance or tissue. |

-continued

| SETUP | LASER OPERATION |
|---|---|
| II. For any dental composite: The operator will use a 300 to 700 μm fiber delivery system. The operator will select from among 300, 360, 400 and 600 μm fiber delivery systems for the recommended embodiment. The proper curing cycle time range is 3 to 5 seconds. Placing the distal end of the delivery fiber out of contact with the composite or in contact or near contact with soft tissue will permit the operator to cut soft tissue and cure composite simultaneously. | Press a foot switch or other activator to activate the laser. |
| III. Photopolymerization using sequential method of operation Place composite into a tooth. Position laser optical fiber perpendicular to the resin-based composite (RBC) within 2 to 6 mm of the RBC on/within tooth And/or additionally or alternatively position laser optical fiber perpendicular to OPPOSITE side and on/or near tooth 25 structure in order to polymerize THROUGH the tooth and polymerize the RBC from its tooth/RBC contact interface And/or additionally or alternatively position the laser optical fiber to the OPPOSITE side of the restoration or tooth to cure through cement-based material. | Press a foot switch or other activator to sequentially activate near-infrared and blue wavelengths and sequentially heat and photopolymerize the RBC. The light is delivered 3-5, 1-6, 4-8, 5-10 second duration cure cycles, with user-selectable timing intervals. |
| IV. Automatically and sequentially after near-infrared selectable duration is complete, the blue wavelength is delivered, with user-selectable timing intervals. Blue light is delivered for 3-5, 5-10 seconds, user-selectable. For any dental composite The operator will use a 300 to 700 μm fiber delivery system. The operator will select from among 300, 360, 400 and 600 μm fiber delivery systems for the recommended embodiment. Placing the distal end of the delivery fiber out of contact with the composite or in contact or near contact with soft tissue will permit the operator to cut soft tissue and cure composite simultaneously. | Press a foot switch or other activator to activate the laser. |
| V. Photopolymerization using overlapping, simultaneous, and sequential methods of operation Place composite into a tooth. Position laser optical fiber perpendicular to the resin-based composite (RBC) within 2 to 6 mm of the RBC on/within tooth And/or additionally or alternatively position laser optical fiber perpendicular to OPPOSITE side and on/or near tooth 25 structure in order to polymerize THROUGH the tooth and polymerize the RBC from its tooth/RBC contact interface And/or additionally or alternatively position the laser optical fiber to the OPPOSITE | Press a foot pedal or other activator to activate near-infrared wavelengths to heat the RBC. Automatically after the near-infrared selectable duration is complete, the blue wavelength is activated simultaneously with the near-infrared and delivered, with user-selectable timing intervals, to heat and photopolymerize the RBC. Near-infrared and blue light is delivered for 1-3, 3-5, 5-10 seconds, with user-selectable timing intervals. Automatically and sequentially after the near-infrared and blue wavelengths selectable duration |

-continued

| SETUP | LASER OPERATION |
|---|---|
| side of the restoration or tooth to cure through cement-based material. | is complete, the blue wavelength is activated sequentially. Blue light is delivered for 3-5, 5-10 seconds, with user-selectable timing intervals. |

While various embodiments of the present invention have been described above, it should be understood that they have been presented by way of example only, and not limitation. It will be apparent to those skilled in the art that various changes in the form and details can be made without departing from the spirit and scope of the invention. As such, the breadth and scope of the present invention should not be limited by the above-described exemplary embodiments but should be defined only in accordance with the following claims and equivalents thereof.

The invention claimed is:

1. A diode lasing device for dentistry and oral surgery, said diode lasing device comprising:

a first laser diode with a wavelength of 450-510 nanometers (nm), with a power range of 0.1 to 2 Watts, wherein said first laser diode is activated for photopolymerization of dental composites with a power range of 0.2 to 0.4 Watt and a pulse rate of 10-30 Hz for 1 to 10 seconds, wherein said first laser diode provides preheating composite, wherein said first laser diode is activated for incising and excising soft tissue with a power range of 0.4 to 1.0 Watt, wherein said first laser diode has an antibacterial and a virucidal application;

a second laser diode with a wavelength of 800-1200 nanometers (nm), with a power range of 0.1 to 3 Watts, wherein said second laser diode is activated for incising and excising soft tissue with a power range of 0.4 to 1.6 Watts, wherein said second laser diode provides preheating composites with a power range of 0.4 to 2 Watts or 5 to 30 seconds, wherein said second laser has said antibacterial application;

a third laser diode with a wavelength of 600-750 nanometers (nm) with a power range of 1 mW to 1 Watt, wherein said third laser diode is activated to provide an aiming beam, wherein said third laser diode provides photobiomodulation;

an optical element, wherein said optical element is configured to combine said first laser diode, said second laser diode, said third laser diode into a single beam, wherein said single beam is used in patient treatment;

a current control, wherein an electrical current passes through at least one laser diode in response to a microprocessor control, wherein said current control is configured to control output power level of said single beam used in said patient treatment, wherein a microprocessor makes a timed or time-phased energy measurement to adjust said electric current flowing through the laser diodes, wherein said microprocessor initiates error messages when said microprocessor senses an error condition that cannot be corrected, wherein said microprocessor initiates a halt to a laser device operation when said microprocessor senses an unsafe condition that cannot be corrected, wherein said microprocessor initiates audible alerts to notify an operator that said laser device operation has been halted, wherein said microprocessor initiates said audible alerts to notify said operator that time periods have elapsed during a composite curing cycle and to prevent overpolymerization, wherein said microprocessor initiates said audible alarms to advise said operator to prevent overenergizing a target substance, wherein said microprocessor initiates said audible alarms to advise said operator to prevent overenergizing a tissue.

2. The diode laser device of claim 1, wherein a sequential emission of laser wavelengths is configured in an overlapping manner during duty cycles to assist an operator in performing procedures.

3. The performing procedures of claim 2, wherein said performing procedures include heating and polymerizing a dental composite in situ upon exposure to emissions from said second laser diode and said first laser diode respectively.

4. The diode laser device of claim 1, wherein photobiomodulation from a non-ionizing visible and an infrared light is configured to alleviate inflammation, enhance immunomodulation, promote wound healing, tissue regeneration upon exposure to emissions from said second laser diode and said third laser diode.

5. The photobiomodulation of claim 4, wherein said non-ionizing visible and said infrared light is configured to upregulate growth factors upon said exposure to emissions from said second laser diode and said third laser diode.

6. The diode lasing device of claim 1, wherein:

said dental composite is cured through a structure of a tooth enamel from outside into a tooth cavity preparation upon said exposure to emissions from said first laser diode.

7. The diode lasing device of claim 1, wherein:

said dental composites are cured through nonmetallic matrix bands including polyester, celluloid and acetate from said outside into a tooth cavity preparation upon said exposure to emissions from said first laser diode.

8. The diode lasing device of claim 1, wherein a ceramic restoration is cured from one side of a veneer through a tooth structure to shrink said composite toward a tooth upon said exposure to emissions from said first laser diode.

9. The diode lasing device of claim 1, wherein:

veneers, crowns, during initial photopolymerization upon said exposure to emissions from said first laser diode, are tack-cured in at least one area to anchor said restoration in place thereby facilitating removal of an interproximally uncured composite prior to final photopolymerization.

10. The diode lasing device of claim 1, wherein:

in a setpoint-controlled operating mode, a duty cycle of said first laser diode is 20% to 65%, wherein said duty cycle of said second laser is diode is 20% to 65%; and an output power of a single beam of said first laser diode is controlled to a particular setpoint via a feedback loop with a power meter, wherein said output power of said single beam of said second laser diode is controlled to said particular setpoint via said feedback loop with said power meter.

11. The diode lasing device of claim 1, wherein:

in a pulsed laser operating mode, said power delivered from a single optical fiber is varied by pulsing of at least one of said first laser diode emissions, said second laser diode emissions at a frequency of 10 Hz to 50 Hz using a 20 to 100 msec pulse width with a 50% duty cycle.

12. The diode lasing device of claim 1, wherein:
at least one of said first laser diode, said second laser diode, said third laser diode emissions are continuous wave emission.

13. The diode lasing device of claim 1, wherein:
for a particular time period energy from said first laser diodes is intermittently delivered from said single optical fiber and a numerical sum of energy delivered from said single optical fiber (Joules) is displayed to an operator, wherein said particular time period energy from said second laser diode is intermittently delivered from said single optical fiber and said numerical sum of energy delivered from said single optical fiber (Joules) is displayed to said operator.

14. The diode lasing device of claim 2 further comprising:
within a diode lasing device housing, a laser power instrument that measures actual power (Watts) to determine whether said power of a single beam emitted from at least one of said first laser diode, said second laser diode, said third laser diode through said single optical fiber equals the displayed power setting.

* * * * *